United States Patent [19]

Ueno et al.

[11] 4,235,992

[45] Nov. 25, 1980

[54] METHOD FOR PRODUCING HIGH PURITY STEROL GLYCOSIDES

[75] Inventors: Masakazu Ueno, Joya; Akira Sano, Otsu; Kyoichi Ideguchi, Kyoto, all of Japan

[73] Assignee: Nippon Shinyaku Co., Ltd., Japan

[21] Appl. No.: 32,275

[22] Filed: Apr. 23, 1979

[51] Int. Cl.³ .............................................. C07J 17/00
[52] U.S. Cl. ...................................... 536/5; 424/180; 424/182
[58] Field of Search ............................ 536/5; 424/182

[56] References Cited

U.S. PATENT DOCUMENTS

| | | | |
|---|---|---|---|
| 2,395,340 | 2/1946 | Marker et al. | 536/5 |
| 3,644,330 | 2/1972 | Eberlein | 536/5 |

FOREIGN PATENT DOCUMENTS 1043029  9/1966  United Kingdom ...................... 536/5

OTHER PUBLICATIONS

Kiribuchi et al., Agr. Biol. Chem. vol., 30, No. 8, pp. 770–778 (1966).

*Primary Examiner*—Johnnie R. Brown
*Assistant Examiner*—Blondel Hazel
*Attorney, Agent, or Firm*—Jacobs & Jacobs

[57] ABSTRACT

A method for producing high purity sterol glycosides which is characterized by selecting a most suitable raw material from among raw materials, by making use of free sterols coexistent in said raw materials, as an indication for the selection; extracting a mixture of sterol glycosides from the selected raw material; turning the resulting extract into their tetracetates; thereafter separating an objective fraction alone according to a liquid chromatography; and hydrolyzing this fraction to obtain the original sterol glycosides.

3 Claims, 1 Drawing Figure

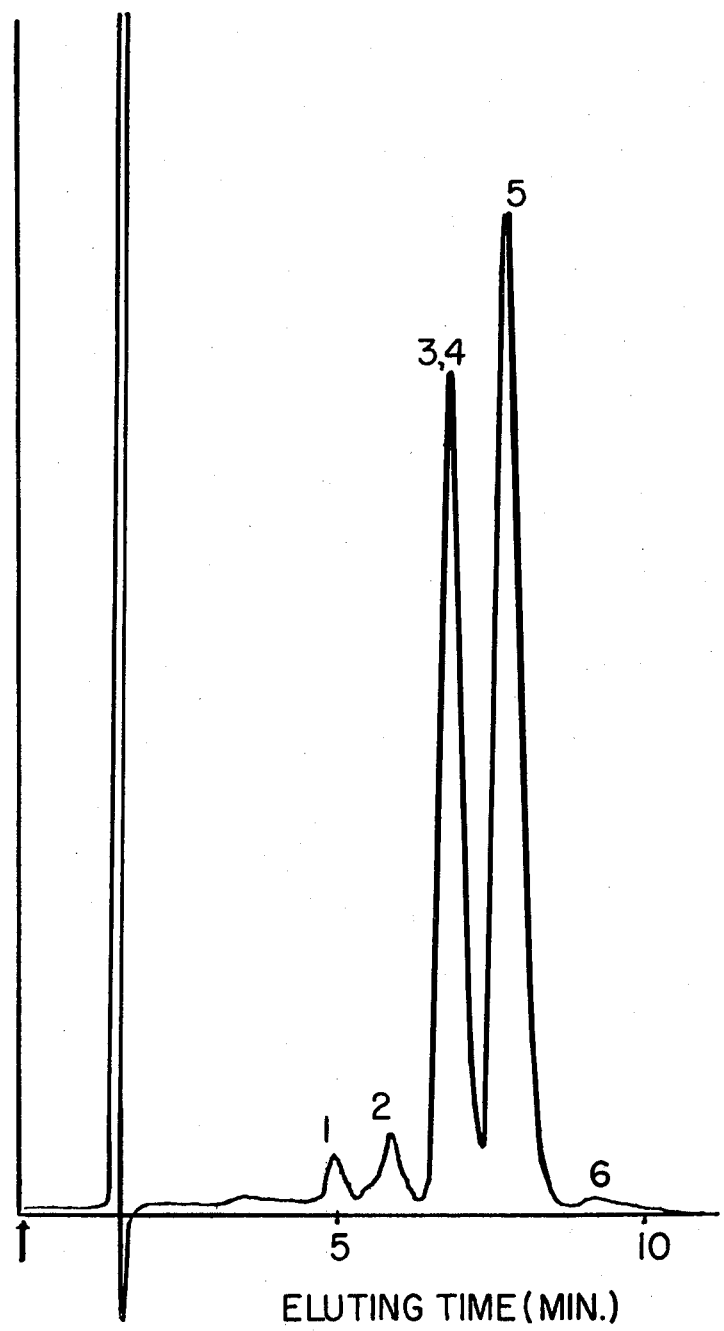

METHOD FOR PRODUCING HIGH PURITY STEROL GLYCOSIDES

DETAILED DESCRIPTION OF THE INVENTION

The present invention relates to a method for rapidly producing in high yield a single sterol glycoside from a mixture of sterol glycosides which originates in natural substances. The sterol glycosides obtained from the present invention have a hemostatic effect and a blood vessel-reinforcing effect and are also useful as a pharmaceutical.

As is already broadly known, the sugar constituent of naturally occurring sterol glycosides is generally glucose, while the sterol constituent usually involve a plurality of extremely similar structures of free sterols which are naturally existent.

Even in the case where it was reported in the past that substances obtained from certain plants were existent in the form of a single sterol glycoside, it has been found a result of gas chromatography-mass spectrometry analysis (hereinafter abbreviated to GC-MS), that these substances invariably contain different kinds of sterol glycosides. Since sterols of sterol glycosides have extremely similar structures, as mentioned above, purification methods such as recrystallization method, various kinds of liquid chromatography, precipitation reactions with alkali metal salts, etc., have only made it possible to separate a mixture of sterol glycosides from other substances in admixture therewith. These methods have not permitted separation of sterol glycosides from each other. Thus, it has been regarded to be difficult to separate a mixture of natural sterol glycosides from each other so as to obtain a pure sterol glycoside, even in small amounts. The present invention provides a separation method according to which it is possible to obtain single sterol glycoside from a mixture of sterol glycosides which originates in natural substances, in a high purity and on a commercial scale.

The present invention will be described below in detail in the order of its procedure.

(1) Selection of raw material

In order to separate and obtain a desired sterol glycoside with certainty, in a high purity and with a high yield, it is necessary to correctly determine the kinds and proportions of the respective constituents of a mixture of sterol glycosides in a raw material, because, even when liquid chromatography as discussed below is applied, the resulting separation has of itself a limitation. Hence it is necessary to select, at the stage prior to the liquid chromatography, a raw material containing no other kinds of sterol glycosides which are difficult to separate from the desired sterol glycoside. Mixtures of sterol glycosides which originate in natural substances are intrinsic of the kinds of said natural substances, and also the kinds and the constitution proportions are infinitely varied and distributed. Accordingly, notwithstanding the separation according to the liquid chromatography as mentioned below has a limitation, it becomes possible to isolate all kinds of sterol glycosides from natural substances, by selecting an adequate raw material.

Depending on the desired sterol glycoside, a detailed analysis of sterol glycosides with a number of raw materials is necessary to identify a raw material which is actually suitable for the purpose. The present inventors have established a method for determining the kinds and proportion of sterols constituting sterol glycosides in a raw material, in a simple manner, correctly and in a short time, and thus have solved this problem.

The method for selecting a raw material is based on such the finding that the kinds and proportion of free sterols which are always coexistent in an objective sample which originates in natural substances accord well with those of sterol glycosides. Heretofore, for example, the analysis of a mixture of sterol glycosides in a plant has been studied through a procedure of firstly extracting a mixture of sterol glycosides, separating and purifying it, thereafter subjecting it to acid decomposition in an alcohol, and analyzing the resulting free sterols. However, such a method not only has been cumbersome in the operation and has required a long time, but also has had a decisive drawback in that, in case of certain kinds of sterols, decomposition thereof occurs during the process of acid treatment, while, in the case of other sterols, isomerization occurs, hence making it impossible to correctly grasp sterol glycosides which are really present. For example, $\Delta^{24(28)}$ sterols, which are naturally broadly distributed, change into compounds having a double bond dislocated, as shown below.

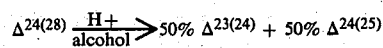

$$\Delta^{24(28)} \xrightarrow{\text{H+}}_{\text{alcohol}} 50\% \, \Delta^{23(24)} + 50\% \, \Delta^{24(25)}$$

Thus, results from which it has seemed as if a difference were present between free sterols and sterol glycosides in the same kind of plant, have often been reported. However, as mentioned below, according to the direct analytical method developed by the present inventors, a correct comparative study on both of the sterols has become possible, and from the results of studies with a number of plants, it has been clearly confirmed for the first time that the kinds and the constitution proportion of both of the sterols accord well. With regard to raw materials obtained from wheat, etc., examples thereof are shown in Table 1.

TABLE 1

Comparison of sterols constituting free sterols with those constituting sterol glycosides

| | | Campe-sterol | Stigma-sterol | β-sitosterol | 24-Methylene-cholesterol | Avena-sterol |
|---|---|---|---|---|---|---|
| Wheat | f. | 22% | —% | 72% | 1% | 5% |
| | G. | 20 | — | 75 | 1 | 4 |
| Rice | f. | 18 | 15 | 63 | 1 | 3 |
| | G. | 15 | 17 | 65 | 0.5 | 2.5 |
| Corn | f. | 23 | 7 | 66 | 1 | 3 |
| | G. | 20 | 9 | 68 | 1 | 2 |
| Soy-bean | f. | 22 | 20 | 54 | 1 | 3 |
| | G. | 23 | 19 | 55 | 1 | 2 |
| Kapok | f. | 9 | 8 | 80 | 0.5 | 2.5 |
| | G. | 10 | 9 | 78 | 0.5 | 2.5 |
| Cotton seed | f. | 4 | — | 95 | — | 1 |
| | G. | 4 | — | 95 | — | 1 |
| Coffee bean | f. | 20 | 21 | 54 | 1 | 4 |
| | G. | 17 | 22 | 57 | 1 | 3 |

(f. represents free sterols and G. represents sterol glycosides.)

The analysis of free sterols does not require any particular treatment such as acid decomposition, etc., as compared with the case of sterol glycosides. In addition, a precise analysis is possible with a small amount of sample, without any particular purification, by means of GC-MS, etc., in a short time, and hence it is possible to soon judge, based on the analytical results of the free sterols, whether the sterol glycosides to be isolated are suitable or not as a raw material. In practice, as for the decision of whether they are suitable or not as raw material, it becomes a standard of the judgement whether $\Delta^5$- and $\Delta^7$-sterol glycosides are in admixture or not. For example, in case where isolation of $\Delta^5$-sterol glycosides is desired, a raw material containing almost no $\Delta^7$-sterol glycosides should be selected, while, in case where isolation of $\Delta^7$-sterol glycosides is desired, a raw material containing no $\Delta^5$-sterol glycosides, such as a number of plants belonging to cucurbitaceae, etc. should be selected.

In case of plants whose sterol compositions have already be sufficiently studied, it is possible to make use of the results as a material for selecting a raw material, but, in case of the present invention wherein isolation of high purity sterol glycosides is aimed, different kinds of sterol glycosides which are difficult to separate should not be present even if their amount is 1% or smaller, and even in case of isolation of representative sterol glycosides illustrated in Examples mentioned below, raw materials have been strictly selected according to the above-mentioned means to achieve the object.

Next, in case where raw materials are taken into account from an economical viewpoint, all raw materials which originate in natural substances and have been presently dealt on a commercial scale are utilizable, and a number and a variety of other substances which are readily available, such as products, oil seed extraction cakes, useless disposal portions, by-products, etc., can be utilized.

(2) Separation of mixture of sterol glycosides and acetylation thereof

Separation of mixture of sterol glycosides from a raw material can be carried out according to known methods, and it is also possible to easily obtain them in a high purity according to a specific precipitation reaction between sterol glycosides and an alkali metal carbonate in a lower alcohol disclosed by the present inventors (Japanese Patent application No. 9996/1975). Although sterol glycosides are difficulty soluble in generally used organic solvents, handling large amounts thereof by means of a number of organic solvents becomes possible by acetylating them into their tetraacetates in a conventional manner, and also it is possible to extend the kinds of mobile phases in liquid chromatography.

(3) Separation of mixture of sterol glycoside tetraacetates by means of liquid chromatography As already described above, there has heretofore been no effective means for separating mixture of sterol glycosides from each other, and separation thereof has been very difficult, but the present inventors, as a result of preliminary studies, have found a means for separating sterol glycoside from each other according to a liquid chromatographical method, and attempted to separate mixture of sterol glycoside tetraacetates according to a liquid chromatography under various conditions. As a result, it has been clarified that stationary phases which are effective for the separation, silica gel silver nitrate-impregnated silica gel, magnesium oxide, alumina, Florisil, etc. exhibit a separating capability to the same extent as that in case of separation of free sterols, and in case of sterol glycosides, too, the separation is very effectively carried out based mainly on the difference in the structures of constituting sterols.

The above-mentioned stationary phase can be employed for the separation of sterol glycosides in all the same manner as in the case where it has so far been applied to free sterols, by selecting a suitable mobile phase solvent.

The present inventors have further made studies on separating conditions which are more practical and hgher in the performance, and as a result, have established a separating method according to a high performance liquid chlormatography (HPLC) wherein a stable microfine silica gel-ODS (a material obtained by chemically bonding octadecyl group to silica gel) is employed as a stationary phase and a single solvent such as methamol, acetonitrile, etc. is employed as a mobile phase. Thus it has become possible for the first time to isolate cholesterol glucoside, brassicasterol glucoside, campesterol glucoside, stigmasterol glucoside, $\beta$-sitosterol glucoside and $\Delta^7$-sterol glycosides and reduction substances, etc. corresponding thereto, from mixtures of sterol glycosides which originate in natural substances, such a separation having been impossible according to other methods. An example of the HPLC chromatogram of sterol glycoside tetraacetates obtained from soyalecithin under these conditions is shown in FIG. 1.

Further, this separation according to HPLC is furnished with all advantageous conditions necessary for scale-up, and a production on a commercial scale is also possible.

(4) Deacetylation

When the resulting single sterol glycoside tetraacetate is subjected to an alkaline alcohol treatment in a conventional manner, a deacetylated, difficultly soluble sterol glycoside quantitatively precipitates from the alcohol and it is possible to easily obtain an objective pure sterol glycoside.

Next, isolation of three kinds of sterol glycosides which are most abundantly present in nature will be described in Example 1, and an example of separation of slightest amounts of sterol glycosides will be described in Example 2.

EXAMPLE 1

Isolation of $\beta$-sitosterol glucoside (I), stigmasterol glucoside (II) and campesterol glucoside (III)

Free sterols contained in acetone-extracts from about 10 kinds of plants were analyzed according to GC-MS, and plants containing almost no $\Delta^7$-sterol-glycoside, such as kapok seed, soybean, olive, corn and wheat, etc. were selected as raw materials suitable for isolation of (I); potato contining amost no (III) which is difficult to separate according to HPLC was selected as a raw material suitable for isolation of (II); and wheat germ containing almost no (II) was selected as a raw material suitable for isolation of (III).

These raw materials are each treated according to the following procedure which is common thereto:

A defatted and dried raw material is extracted twice with acetone in an amount of twice volume based on the weight of the raw material, and then acetone is distilled off. 10% KOH methanol in an amount of 20 times volume based on the weight of the residue is added. After reflux for one hour, $K_2CO_3$ is added till saturation is a attained, and successively reflux is carried out for 3 hours. The resulting precipitate is washed with methanol and then with water and dried to obtain a mixture of high purity sterol glycosides, which are then converted to their tetraacetates with acetic anhydride in pyridine in a conventional manner. The tetraacetates are employed as samples for separation according to HPLC. Conditions of HPCL are as follows:

Stationary phase: Silca gel-ODS (5μ) (column, 10 mmφ×30 cm)

Mobile phase: acetonitrile (flowrate, 10 ml/min)

Under these condition, the amount of sample once treated is 0.1 g and the time required is within 10 minutes. In such once separation, the objective substance could be completely isolated from each sample without any loss of the substance. Tetraacetates corresponding to the resulting isolated (I)–(III) are collectively described in Table 2 together with those obtained in Example 2.

By hydrolyzing the tetraacetates with 5% KOH methanol, sterol glycosides quantitatively precipitated from methanol and pure sterol glycosides could be easily obtained.

EXAMPLE 2

Separation of 24-methylenecholesterol glycoside (IV) and avenasterol glycoside (V)

(IV) and (V) are generally present in mixtures of sterol glycosides as a small amount component. In this Example, a commercial soyalecithin was employed as a raw material, and sterol glycosides were separated therefrom, utilizing a precipitation reaction with $K_2CO_3$ in methanol (said Japanese Patent Application No. 9996/1975), and purified and further turned into tetraacetates, to prepare separation samples (IV) and (V). (IV) and (V) contained therein can be separated by direct by applying HPLC, but the resulting efficiency is inferior. Thus they were subjected to a column chromatography employing a silver nitrate-impregnated silica gel as a stationary phase, and main sterol glycosides (I)–(III) initially flowing out were removed to obtain a mixture consisting mostly of tetraacetates of (IV) and (V), alone, which were then employed as samples for HPCL. In the separation according to the column chromatography with a silver nitrate-impregnated silica gel, a 20% silver nitrate-impregnated silica gel (4 cm×40 cm) was employed as a stationary phase and chloroform/cyclohexane (5:1) were employed as a mobile phase solvent, and once 5 g of a sample was treated to obtain about 1 g of a mixture of tetraacetates of (IV) and (V) from 25 g of the sample. Next, employing this mixture as a sample, separation accroding to HPCL was carried out under the conditions of Example 1 to separate (IV) and (V) from each other.

In addition, according to purity assay through HPLC and GC, it was confirmed that a product having a purity of 99% or higher was obtained for (IV) and a product having a purity of 97% or higher was obtained for (V). Separated tetraacetates are summarized in Table 2. Separated tetraacetates were simply deacetylated with 5% KOH-methanol, and the corresponding amounts of sterol glycosides precipitated quantitatively.

TABLE 2

| | Observed values of isolated tetraacetates | | | | |
|---|---|---|---|---|---|
| | | | Elemental analysis | | |
| Isolated Substance | Yield (g)* | Melting point(C°) | (upper, observed value; C, | lower, calculated value) H | Purity through HPLC and GC |
| β-sitosterol glucoside | | 175–177 | 69.48 | 9.31 | 99 or higher % |
| | | | 69.32 | 9.20 | |
| Stigmasterol glucoside | 0.40 | 128–130 | 69.60 | 8.91 | 99 or higher % |
| | | | 69.54 | 8.89 | |
| Campesterol glucoside | 0.18 | 172–174 | 68.97 | 9.29 | 99 or higher % |
| | | | 69.01 | 9.10 | |
| 24-Methylene-cholesterol glucoside | 0.41 | 166–168 | 69.03 | 8.98 | 99 or higher % |
| | | | 69.23 | 8.80 | |
| Avenasterol glucoside | 0.48 | 181–183 | 69.32 | 9.14 | 97 or higher % |
| | | | 69.54 | 8.89 | |

*Yield obtained by treating 1g of sample through HPLC

BRIEF DESCRIPTION OF THE DRAWING

FIG. 1 represents a high performance liquid chromato-gram of sterol glucoside tetraacetates of soyalecithin. The abscissa represents the eluting time and the ordinate represents the height of the peaks. Silica gel-ODS (4 mm×30 cm) was employed as column; the amount of sample pourred in was 10 mg; acetonitrile was employed as mobile phase; the pressure was 50 kg/cm$^2$; the flow rate was 1.3 ml/min; a refractometer was employed as detector; and the measurement temperature was 25° C. Peak 1 represents 24-methylenecholesterol glucoside tetraacetate; numeral 2, avenasterol glucoside tetraacetate; peak 3, stigmasterol glucoside tetraacetate; peak 4, campesterol glucoside tetraacetate; peak 5, β-sitosterol glucoside tetraacetate; and peak 6, stigmastanol glucoside tetraacetate, respectively.

What is claimed is:

1. In the method of separating individual sterol glycosides from one another in high purity from a raw material containing said sterol glycosides, the steps which comprise treating an extract of said raw material containing said sterol glycosides with an acetylating agent to produce the corresponding sterol glycoside tetraacetates, subjecting said acetylated extract to liquid chromatography to separate the individual sterol glycoside tetraacetates, and hydrolysing the separated tetraacetate of the desired sterol glycoside under basic conditions to produce the desired individual sterol glycoside.

2. The method according to claim 1 wherein said raw material is derived from wheat, rice, corn, soybean, kapok, cottonseed or coffee bean.

3. The method according to claim 1 wherein said desired individual sterol glycoside is selected from the group consisting of campesterol glucoside, stigmasterol, glucoside, β-sitosterol glucoside, 24-methylenecholesterol glucoside and avenasterol glucoside, said desired individual sterol glycoside being in admixture in said raw material with at least one other sterol glycoside selected from said group.

* * * * *